United States Patent [19]

Marette

[11] Patent Number: 5,721,386
[45] Date of Patent: Feb. 24, 1998

[54] INSTALLATION FOR INSPECTING COMPACT DISCS

[75] Inventor: Gilles Marette, Coulommiers, France

[73] Assignee: Societe d'Exploitation des Machines Dubuit, Noisy le Grand, France

[21] Appl. No.: 728,252

[22] Filed: Oct. 8, 1996

[30] Foreign Application Priority Data

Oct. 23, 1995 [FR] France ............................. 95 12433

[51] Int. Cl.$^6$ ...................................................... G01B 11/00
[52] U.S. Cl. ............................ 73/865.8; 209/538; 209/701
[58] Field of Search ............................ 73/865.8; 209/509, 209/538, 542, 540, 553, 698, 701; 194/411

[56] References Cited

U.S. PATENT DOCUMENTS

| | | | |
|---|---|---|---|
| 3,901,381 | 8/1975 | Quinn | 209/701 |
| 3,991,883 | 11/1976 | Hobler et al. | 209/538 |
| 4,497,409 | 2/1985 | Chong | 209/538 |
| 4,643,027 | 2/1987 | Deutsch et al. | 73/865.8 |
| 4,826,019 | 5/1989 | Kondo et al. | 209/538 |
| 4,852,415 | 8/1989 | Bogatzki et al. | 73/865.8 |
| 4,863,039 | 9/1989 | Kondo et al. | 209/538 |
| 4,954,723 | 9/1990 | Takahashi et al. | 250/572 |
| 5,232,505 | 8/1993 | Noval et al. | 118/712 |
| 5,411,588 | 5/1995 | Diepens et al. | 118/666 |
| 5,520,107 | 5/1996 | Airoldi | 101/35 |
| 5,549,444 | 8/1996 | Dubuit | 414/796.7 |
| 5,549,544 | 8/1996 | Young et al. | 601/2 |

FOREIGN PATENT DOCUMENTS 0528106  2/1993  European Pat. Off. .
0574975  12/1993  European Pat. Off. .

*Primary Examiner*—Robert Raevis
*Attorney, Agent, or Firm*—Young & Thompson

[57] ABSTRACT

An installation for inspecting compact discs includes a transfer turntable rotatable stepwise about an axis and mobile along that axis on each step with a plurality of transfer units carried by the transfer turntable which alternately pick up and put down a compact disc to be inspected. A plurality of action stations at the periphery of the transfer turntable include a loading station, at least two inspection stations, at least one reject station and an offloading station.

19 Claims, 2 Drawing Sheets

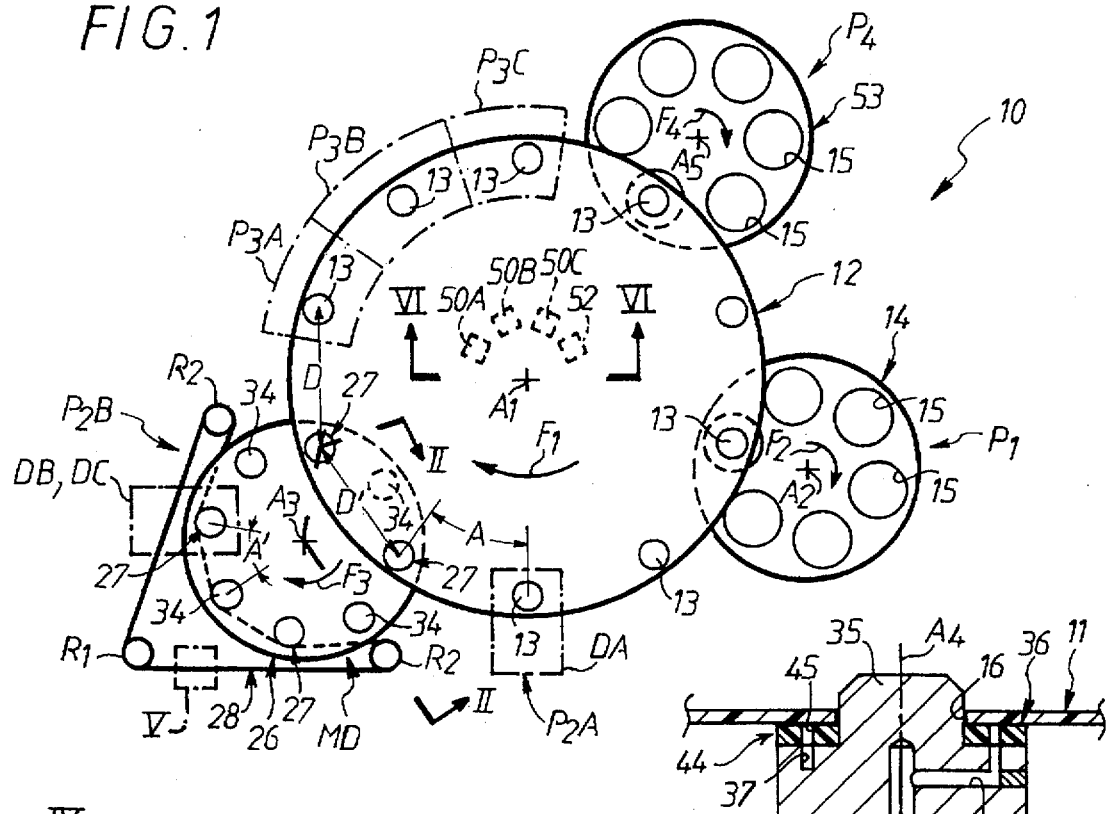
FIG.1
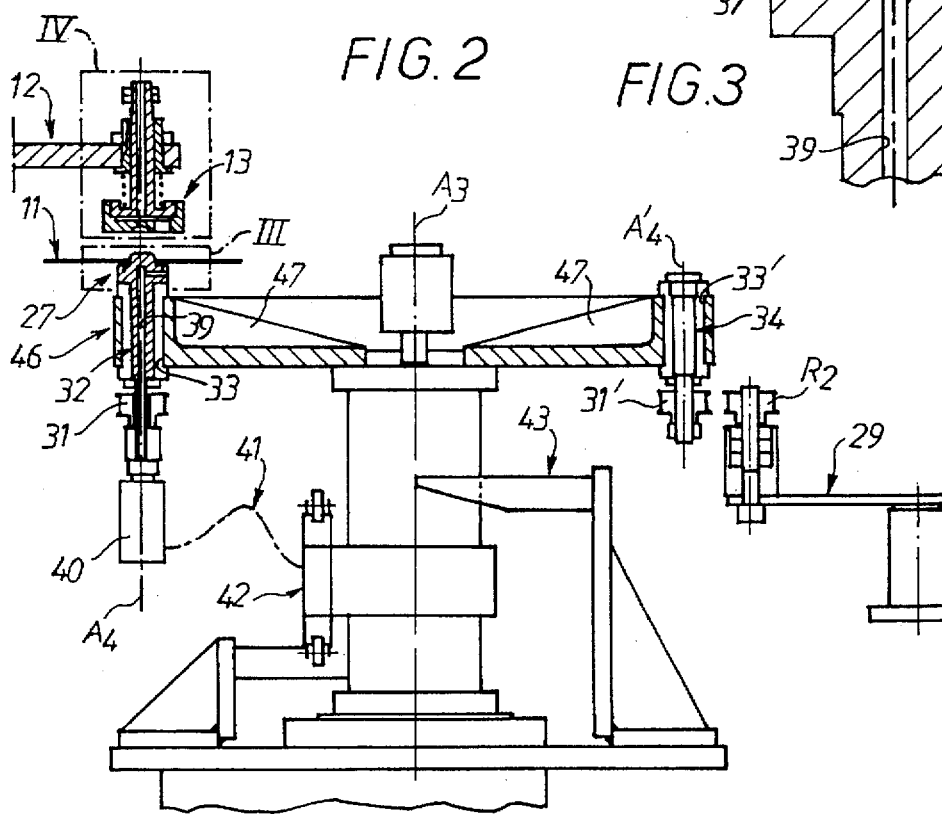
FIG.2
FIG.3

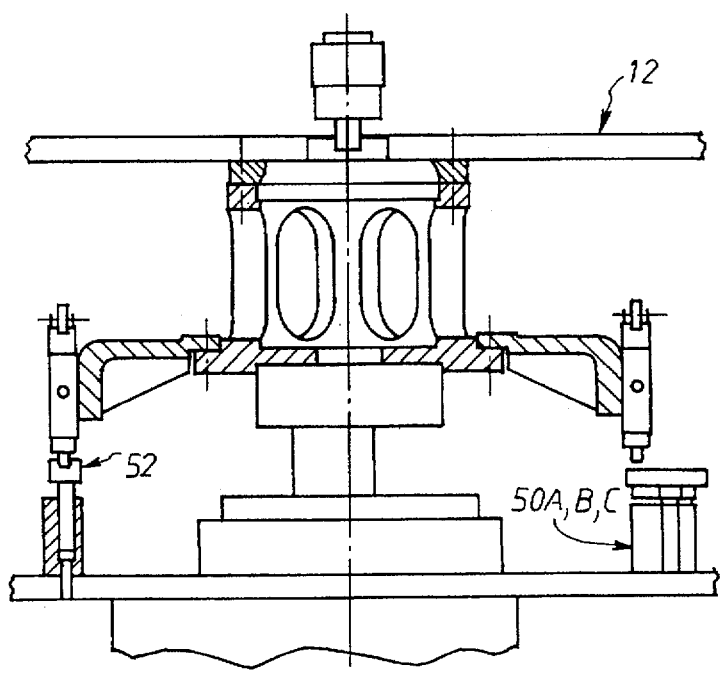
FIG. 6
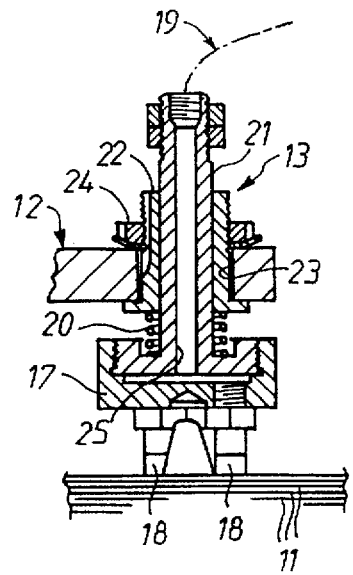
FIG. 4
FIG. 5
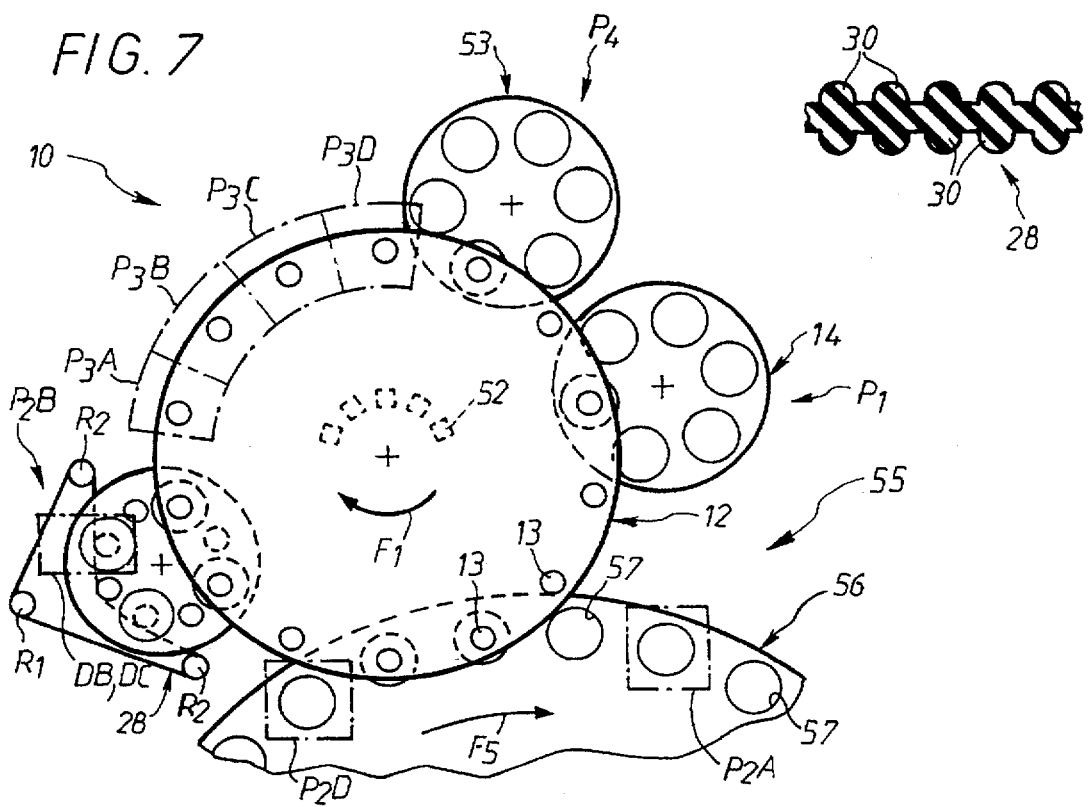
FIG. 7

INSTALLATION FOR INSPECTING COMPACT DISCS

BACKGROUND OF THE INVENTION

1. Field of the Invention

The present invention concerns the inspection of compact discs that is usually required after their manufacture.

2. Description of the Prior Art

The features of the compact discs checked are the recording, the identifying code usually allocated to them to facilitate their subsequent computer processing, whether this is an alphanumeric code or a bar code, and possibly the information and/or decoration printed on them, if the printing has not previously been inspected elsewhere.

For high productivity these inspections must naturally be carried out automatically.

The present invention consists in an inspection installation meeting this requirement.

SUMMARY OF THE INVENTION

This inspection installation includes a transfer turntable rotatable stepwise about an axis and moveable to and fro along said axis on each step, a plurality of transfer units carried by said transfer turntable, circumferentially distributed about its axis and each adapted alternately to take up and to put down a compact disc to be inspected, a plurality of action stations at the periphery of said transfer turntable at least partly vertically aligned with the path of said transfer units carried by the latter, including a loading station that is fed with compact discs to be inspected, at least two inspection stations at each of which said compact discs to be inspected are each subjected in turn to at least one individual inspection, at least one reject station at which a compact disc that does not pass inspection is released and an offloading station at which a compact disc that has passed all the inspections is released, and circulation means adapted to receive a compact disc to be inspected from a transfer unit of said transfer turntable, to convey said compact disc to a position in vertical alignment with at least one inspection device, and to rotate said compact disc on itself when it is in vertical alignment in this way with an inspection device and thereafter to return it to a position in line with a transfer unit of said transfer turntable to be taken up again by the latter.

In a first embodiment, the inspection installation may be used autonomously.

It then comprises in an autonomous manner all of the action stations required.

In a different second embodiment, however, the inspection installation of the invention may be used on the output side of a printing machine, continuously with the latter, its transfer turntable then overlying at least locally the conveyor provided with object-stations that a printing machine of this kind usually includes.

In this case, at least one of the inspection stations can be on the printing machine, for example the code inspection station.

In all cases, whether it is used autonomously or in series with a printing machine, the inspection installation of the invention advantageously operates in such a manner that only compact discs passing all of the inspections carried out arrive at its offloading station.

Apart from the fact that the inspection installation of the present invention can therefore be used either as an autonomous unit or as a unit operating in conjunction with a printing machine, it has features and advantages that will emerge from the following description given by way of example with reference to the accompanying diagrammatic drawings.

BRIEF DESCRIPTION OF THE DRAWINGS

FIG. 1 is a plan view to a relatively smaller scale showing the relative disposition of various components of a first embodiment of the inspection installation of the invention.

FIG. 2 is a partial view of two of the components in axial section taken along the broken line II—II in FIG. 1, to a relatively larger scale. FIGS. 3, 4 respectively show to a relatively larger scale the details III, IV in FIG. 2.

FIG. 5 shows to a relatively larger scale the detail V of FIG. 1.

FIG. 6 is a partial view in axial section on the line VI—VI in FIG. 1 of one of the components of the inspection installation of the invention, to a different scale.

FIG. 7 is a plan view similar to that of FIG. 1 relating to a second embodiment of the inspection installation of the invention.

DETAILED DESCRIPTION OF THE PREFERRED EMBODIMENTS

As shown in the figures, the inspection installation 10 of the invention is for processing compact discs 11 with a central opening 16 that may be offered up in a stack.

It includes a circular contour transfer turntable 12 which rotates stepwise about an axis A1, in practise a vertical axis, and which reciprocates along this axis A1 on each step. The transfer turntable 12 carries a plurality of transfer units 13 equi-angularly spaced around its axis A1 and each adapted alternately to pick up a compact disc 11 to be inspected and to put it down, and a plurality of action stations P at the periphery of the transfer platform 12, at least partly vertically aligned with the path of the transfer unit 13 carried by the latter. The stations P include a loading station P1 fed with compact discs 11 to be inspected, at least two inspection stations P2A, P2B at each of which the compact discs 11 to be inspected are each in turn subject to at least one individual inspection, at least one reject station P3A at which a compact disc 11 that does not pass inspection is put down, and an offloading station P4 at which a compact disc 11 that has passed each inspection is put down.

In the embodiment specifically shown in FIG. 1, the inspection installation 10 of the invention operates autonomously and therefore includes in an autonomous manner all of the action stations P.

If the compact discs 11 to be inspected have had printing previously applied to them, which is usually the case in practise, it is assumed here that the printing has already been inspected, and that it is therefore printed compact discs 11 that are presented to the loading station P1.

Other inspections remain to be carried out, however.

There is, first of all, an inspection applying to one or both of the identification codes, an alphanumeric code and a bar code in this case, which the compact discs 11 usually carry for subsequent computer processing.

There is then, and most importantly, an inspection applying to the recording.

The corresponding inspection devices are not relevant to the present invention and for this reason will not be described here.

They use video cameras, for example.

As shown in FIG. 1, there is therefore an inspection device DA for one of the identification codes, an inspection device DB for the other code and an inspection device DC for the recording.

The various inspection devices are divided between the various inspection stations P2.

In the embodiment shown in FIG. 1 there are only two inspection stations P2, P2A, P2B in this case, at an angular distance from each other.

The inspection device DA operates at the inspection station P2A that is more upstream in the direction of rotation of the transfer turntable 12 shown by an arrow F1 in FIG. 1 and the inspection devices DB, DC operate conjointly at the more downstream inspection station P2B, being disposed on substantially the same vertical line, for example.

In this embodiment three reject stations P3A, P3B, P3C are provided in succession, at an angular distance from each other, downstream of the more downstream inspection station P2B.

The reject station P3A corresponds to the compact discs 11 identified as defective by the inspection device DA, for example, the reject station P3B to those identified as defective by the inspection device DB and the reject station P3C to those identified as defective by the inspection device DC.

The various reject stations P3 could be distributed in some other way, however.

At least one of them may additionally correspond to compact discs 11 identified as defective by both of at least two of the inspection devices DA, DB, DC.

A loader 14 is provided at the loading station P1.

The loader 14 is of the type described in U.S. Pat. No. 5,549,444, for example.

As the loader 14 is not in itself relevant to the present invention it will not be described here.

Suffice to say that it rotates about an axis A2 parallel to the axis A1 of the transfer turntable 12, for example in the same direction as the latter, as shown by the arrow F2 in FIG. 1, and that it has a plurality of object stations 15 equi-angularly distributed about the axis A2 and each adapted to receive a stack support, not shown, loaded with a stack of compact discs 11 to be inspected.

The transfer members 13 are also of the type described in U.S. Pat. No. 5,549,444.

They are suction devices, their lower surface being provided with suction means for this purpose.

To be more precise, and as can be seen more clearly for one of them in FIG. 4, they each include a head 17 which carries on its bottom surface a plurality of suction nozzles 18 equi-angularly distributed around its axis, for example three such nozzles which communicate with a pipe 19, as shown in dashed outline in FIG. 4, by which the system can be connected to a suction source, not shown.

The pipe 19 for each of the transfer units 13 is controlled by appropriate valve means.

As shown here, each of the transfer units 13 is preferably mobile on the transfer turntable 12, parallel to the axis A1 of the latter, against return spring means 20 which urge them at all times towards the action stations P.

The head 17, which is under the transfer turntable 12, is in practise carried by a rod 21 slidably mounted in a bush 22 passing through a bore 23 in the turntable and the return spring means 20, which are in the form of a coil spring, for example, as shown here, are operative in compression between the head 17 and the bush 22.

The rod 21 is a shouldered rod, for example, as shown here, and is clamped to the transfer turntable 12 by a nut 24.

It is a hollow rod with an axial bore 25 through which the suction nozzles 18 communicate with the associated pipe 19.

In the embodiment shown in FIG. 1 the transfer turntable 12 has ten identical transfer units 13 equi-angularly spaced with the same angular pitch A about the axis A1.

As already mentioned, the transfer turntable 12 rotates stepwise on a base through which it is mobile vertically to and fro along its axis A1 relative to the frame of the system.

These provisions are familiar to the person skilled in the art and for this reason will not be described here.

The transfer turntable 12 is rotated stepwise by an indexing device, for example.

At one of the inspection stations P2 at least, in this example the more downstream inspection station P2B, in accordance with the invention the inspection installation 10 includes circulation means MD adapted to receive a compact disc 11 to be inspected from a transfer unit 13 on the transfer turntable 12, to move that compact disc 11 to a position vertically in line with at least one inspection device, in this example the two inspection devices DB, DC, to rotate the compact disc 11 about the axis of its central opening 16 when it is vertically aligned with an inspection device in this way, and then to move it into alignment with a transfer unit 13 on the transfer turntable 12 to be taken up again by the latter.

In the embodiment shown the circulation means MD comprise a circulation turntable 26 rotating stepwise about an axis A3 parallel to the axis A1 of the transfer turntable 12, synchronized with the latter and having a plurality of receiver units 27 distributed circumferentially around the circulation turntable 26, projecting from its top surface and each adapted to receive a compact disc 11 to be inspected, and at least one inspection device DB, DC, in this example both inspection devices DB, DC, at the periphery of the circulation turntable 26.

Like the transfer turntable 12, the circulation turntable 26 is rotated stepwise by an indexing device, for example.

It rotates in the same direction as the transfer turntable 12, for example, as shown by an arrow F3 in FIG. 1.

In the embodiment shown, and as is more clearly visible for one of them in FIG. 2, each of the receiver units 27 is rotatably mounted on the circulation turntable 26, rotating about an axis A4 parallel to the axis A3 of the circulation turntable 26 and therefore parallel to the axis A1 of the transfer turntable 12, in order to impart rotation to the compact disc 11 to be inspected vertically aligned with the inspection devices DB, DC concerned, and thus to move the whole of the compact disc 11 into line with the latter.

In the embodiment shown the receiver units 27 are rotated by a fixed notched belt 28 passing in a closed loop around at least two rotary members, including a drive member R1 keyed to rotate with a drive shaft, not shown, and at least one direction changer member R2 rotatably mounted on a boom 29 and with which the receiver units 27 are engaged in turn "on the fly".

In practise there are two direction changer units R2, one on the upstream side and one on the downstream side, and with the drive member R1 they delimit a triangle.

In the embodiment shown the notched belt 28 has teeth 30 on both faces and the receiver units 27 operate outside the loop that it forms.

In practise each of the receiver units 27 is keyed to rotate with a gear 31 through which it meshes with the notched belt 28.

To be more precise, in the embodiment shown, each of the receiver units 27 is carried by a rod 32 which passes through a bore 33 in the circulation turntable 26 and is rotatable about its axis A4 and to which the gear 31, which is located under the circulation turntable 26, is keyed to rotate.

To facilitate the meshing of the gear 31 with the notched belt 28 during the rotation of the circulation turntable 26, the more upstream direction changer unit R2 is coupled to an elastic tensioning device, not shown.

The arm of the boom 29 that carries it constitutes an elastic tensioning device, for example.

In practise the receiver units 27 are equi-angularly distributed about the axis A3 of the circulation turntable 26, with the same angular pitch A'.

By design, the linear distance D' between two successive receiver units 27 on the circulation turntable 26 and that D between two successive transfer units 13 on the transfer turntable 12 are multiples of the same module.

In the embodiment shown, this multiple is equal to one for both the linear distances D, D'.

In other words, the linear distance D' between successive receiver units 27 on the circulation turntable 26 is equal to that D between two successive transfer units 13 on the transfer turntable 12.

In the embodiment shown there are four receiver units 27 and so on each step the circulation turntable 26 rotates 90°.

To minimize the tilting torque that they cause to be exerted on the circulation turntable 26 when they engage with the notched belt 28 and therefore to retain the desirable flatness of the circulation turntable 26, in the embodiment shown the receiver units 27 alternate with direction changer members 34 which also engage in turn, on the fly, with the notched belt 28 and which therefore advantageously reduce the slackness of the latter.

In practise these direction changer members 34 essentially comprise a solid rod, shouldered in the upper part, passing through a bore 33' in the circulation turntable 26, rotatable about an axis A'4 parallel to the axis A3 of the circulation turntable 26 and to which a gear 31' is keyed under the circulation timetable 26.

To center the compact discs 11 to be inspected, each of the receiver units 27 has a boss 35 projecting axially from its top surface, beveled to facilitate engaging the central opening 16 of the compact disc 11.

To improve the stability of the compact discs 11 when they are inspected, each of the receiver units 27 is provided with suction means 36 on its top surface.

In the embodiment shown the suction means 36 include an annular groove 37 in the top surface of a receiver unit 27, around its boss 35, which communicates via at least one radial passage 38 with an axial bore 39 provided for this purpose in the rod 32. Through the intermediary of a rotary joint 40, the axial bore 39 communicates with a pipe 41 shown in chain-dotted line in FIG. 2 and through which the system can be connected to a suction source, not shown.

The pipe 41 for each receiver unit 27 is controlled by valve means 42 and these are actuated on the fly by a cam 43 carried by the frame of the system.

In the embodiment shown, the suction means 36 also include a flexible material washer 44 for each of the receiver units 27 attached to the top surface of the receiver unit 27 around the boss 35 and including a plurality of bores 45 circumferentially distributed and vertically aligned with the groove 37, for improved distribution of the suction.

In the embodiment shown, the rod 32 of the receiver unit 27 passes through a thicker annular rim 46 of the circulation turntable 26 and the circulation turntable 26 is stiffened by radiating stiffener ribs 47.

The overall result of this is to make the top surface of the receiver unit 27 and therefore the compact discs 11 to be inspected more level.

In the embodiment shown, and as seen more clearly in FIG. 5, the teeth 30 on the notched belt 28 are rounded teeth, which provides the best meshing conditions for the receiver units 27, removing all risk of the pinion 31 suddenly escaping from a tooth 30 on coming into contact with the notched belt 28.

Thus the inspection carried out at the inspection station P2B is carried out with the compact discs 11 level and stable.

Further, as the notched belt 28 is operative on the upstream side of the inspection devices DB, DC, the compact disc 11 to be inspected is advantageously run up to speed progressively, to the benefit of the regularity of its rotation speed during inspection.

To be brief, the circulation means MD provided in accordance with the invention have the advantage of rotating the compact disc 11 during inspection with great precision from the mechanical point of view and from the point of view of its speed of rotation, so enhancing the quality of the inspection carried out.

At each of the reject stations P3A, P3B, P3C is a fixed rod vertically in line with the transfer turntable 12 around which the rejected compact discs 11 are successively stacked, with their central opening 16 threaded over it.

The reject discs are in practise rejected by cylinders 50A, 50B, 50C respectively controlled by the inspection devices DA, DB, DC and operating at the appropriate time on the fly on the valve means controlling the pipe 19 of the transfer units 13 when, carrying a compact disc 11 previously identified as defective, a transfer unit 13 arrives at the reject station P3A, P3B, P3C concerned.

Similarly, a fixed peg 52 is provided at the offloading station P4 after the cylinders 50A, 50B, 50C to systematically offload each compact disc 11 reaching the offloading station P4 on the fly.

As described in U.S. Pat. No. 5,549,444 the offloading station P4 is in practise equipped with an offloading device 53 with object-holders 15 which, of a type similar to the loader 14 at the loading station P1, also rotates about an axis A5 parallel to the axis A1 of the transfer turntable 12, for example in the same direction as the latter, as shown by the arrow F4 in FIG. 1.

On each step of the transfer turntable 12 a transfer unit 13 on the latter takes up a compact disc 11 from the loader 14, puts down a compact disc 11 on a receiver unit 27 of the circulation turntable 26 and takes up another compact disc 11 from another receiver unit 27 on the circulation turntable 26.

As already mentioned above, the compact discs 11 carried by the transfer units 13 of the transfer turntable 12 are then either rejected at the reject stations P3A, P3B, P3C or offloaded at the offloading station P4.

In the meantime, they have been inspected in various ways, either on the fly as at the more upstream inspection station P2A or during a cycle of rotation of the circulation turntable 26, as at the more downstream inspection station P2B.

In the alternative embodiment shown in FIG. 7 the inspection installation 10 of the invention is on the output side of a printing machine 55 and operates continuously with it.

Its transfer turntable 12 therefore overlies at least locally the conveyor 56 provided with object-stations 57 that a printing machine 55 of this kind usually includes.

In the embodiment shown, the conveyor 56 is also formed by a circular contour turntable rotating stepwise about an axis parallel to the axis A1 of the transfer turntable 12 and each of its object-stations 57 is adapted to receive directly a compact disc 11 to be printed.

As shown by an arrow F5 in FIG. 7, the conveyor 56 rotates in the opposite direction to the transfer turntable 12.

In an embodiment of this kind at least one of the inspection stations P2 is on the printing machine 55.

Here it is the inspection station P2A relating to one of the identification codes.

A printing inspection station P2D is provided on the printing machine 55, at a distance from the inspection station P2A.

Other features are globally the same as those previously described.

In this embodiment, however, there are four reject stations P3A, P3B, P3C, P3D to allow for the inspection of the printing carried out at the inspection station P2D.

Further, the loading station P1 is obviously fed with unprinted compact discs 11, the feeding of the printing machine 55 with compact discs 11 to be printed and the taking up of compact discs 11 printed on the printing machine 55 being effected by the transfer turntable 12.

Of course, the present invention is not limited to the embodiments described and shown, but encompasses any variant execution thereof.

There is claimed:

1. An installation for inspection of compact discs comprising a transfer turntable rotatable stepwise about an axis and movable to and fro along said axis in unison with the stepwise rotation of the turntable, a plurality of transfer units carried by said transfer turntable along a path of movement, a plurality of circumferentially spaced action stations disposed at the periphery of said transfer turntable adapted alternately to take up and to put down a compact disc to be inspected, said plurality of action stations being at least partly vertically aligned with the path of movement of said transfer units, said plurality of action stations including a loading station to be fed with compact discs to be inspected, at least two inspection stations, each for inspecting each of the compact discs, at least one reject station for releasing any compact disc which does not pass inspection, and offloading station for offloading compact discs which have passed inspection, and circulation means for receiving from one of said transfer units a compact disc to be inspected and for conveying the received compact disc to a position in a vertical alignment with at least one inspection device and to rotate the received compact disc about its axis when in vertical alignment with said at least one inspection device and after inspection by said at least one inspection device for returning the compact disc to a position in line with said one transfer unit to be taken up by said one transfer unit.

2. The inspection installation as claimed in claim 1, wherein the circulation means includes a circulation turntable rotatable stepwise about an axis parallel to the axis of said transfer turntable and synchronized with said transfer turntable, a plurality of receiver units circumferentially arranged on said circulation turntable and projecting from a top surface thereof, each of said receiver units being adapted to receive a compact disc to be inspected and at least one of said inspection devices being disposed at the periphery of said circulation turntable.

3. The inspection installation as claimed in claim 2, wherein each of said receiver units is rotatable about an axis parallel to the axis of said transfer turntable.

4. The inspection installation as claimed in claim 3, further comprising a fixed notched belt successively engageable with said receiver units for rotating the same, said belt defining a closed loop and extending around at least two rotary members, one of said rotary members being a drive member and at least the other of said rotary members being a direction changer member.

5. The inspection installation as claimed in claim 4, wherein said receiver units alternate with said direction changer members, said direction changer members being engaged on the fly with said notched belt.

6. The inspection installation as claimed in claim 4, wherein each of said receiver units is constrained for rotation with a gear meshing with said notched belt.

7. The inspection installation as claimed in claim 4, wherein said notched belt is located upstream of an associated one of said inspection devices.

8. The inspection installation as claimed in claim 4, wherein said notched belt defines a loop and includes teeth on opposed faces thereof, said receiver units being disposed outwardly of the loop.

9. The inspection installation as claimed in claim 4, wherein said notched belt has round teeth.

10. The inspection installation as claimed in claim 4, wherein there are at least two said direction changer members, one of said direction changer members having an upstream location, an elastic tensioning device acting on said one of said direction changer members.

11. The inspection installation as claimed in claim 10, wherein said linear distance between two successive receiver units is equal to the linear distance between two successive transfer units.

12. The inspection installation as claimed in claim 2, wherein the linear distance between two successive receiver units on said circulation turntable and the linear distance between two successive transfer units on said transfer turntable are multiples of a common module.

13. The inspection installation as claimed in claim 2, wherein each of said receiver units has suction means on the top surface thereof.

14. The inspection installation as claimed in claim 2, wherein each of said receiver units having a boss projecting axially from the top surface thereof.

15. The inspection installation as claimed in claim 1, wherein each of said transfer units has suction means on a bottom surface thereof.

16. The inspection installation as claimed in claim 1, wherein each said transfer unit is movable parallel to the axis of said transfer table, spring means biasing said transfer units toward respective said action stations.

17. The inspection installation as claimed in claim 1, wherein said inspection installation is independently operable and said inspection stations are likewise independently operable.

18. The inspection installation as claimed in claim 17, wherein said transfer table at least partly overlies a conveyor object stations of the printing machine.

19. The inspection installation as claimed in claim 1, wherein said inspection installation is disposed on an output side of the printing machine printing compact discs, said at least one inspection station being located in the printing machine for inspecting printing on the compact discs.

* * * * *